US012582844B2

(12) United States Patent
Koehl et al.

(10) Patent No.: US 12,582,844 B2
(45) Date of Patent: Mar. 24, 2026

(54) RADIATION THERAPY SYSTEM WITH FOLLOW-THE-LIGHTS USER INTERFACE

(71) Applicant: Varian Medical Systems, Inc., Palo Alto, CA (US)

(72) Inventors: Susan Koehl, Henderson, NV (US); Ross Hannibal, Saratoga, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 966 days.

(21) Appl. No.: 17/830,347

(22) Filed: Jun. 2, 2022

(65) Prior Publication Data

US 2022/0362581 A1     Nov. 17, 2022

Related U.S. Application Data

(63) Continuation of application No. 16/928,022, filed on Jul. 14, 2020, now Pat. No. 11,358,006, which is a
(Continued)

(51) Int. Cl.
*A61N 5/10*        (2006.01)
*A61B 6/46*        (2024.01)
(Continued)

(52) U.S. Cl.
CPC ............ *A61N 5/1048* (2013.01); *A61B 6/461* (2013.01); *A61B 6/467* (2013.01); *H01H 9/161* (2013.01); *H01H 13/023* (2013.01); *H01H 13/70* (2013.01); *H05G 1/56* (2013.01); *H05G 1/58* (2013.01); *A61B 6/0487* (2020.08); *A61B 2017/00017* (2013.01); *A61B*

*2017/00199* (2013.01); *A61N 2005/1074* (2013.01); *A61N 5/1081* (2013.01); *H01H 2013/026* (2013.01); *H01H 2239/006* (2013.01); *H01H 2239/064* (2013.01); *H01H 2300/014* (2013.01);
(Continued)

(58) Field of Classification Search
None
See application file for complete search history.

(56) References Cited

U.S. PATENT DOCUMENTS 4,670,006 A      6/1987  Sinnett et al.
6,032,066 A  *   2/2000  Lu ........................ A61N 5/1049
                                                    378/65
(Continued)

*Primary Examiner* — Thaddeus B Cox
(74) *Attorney, Agent, or Firm* — SU IP CONSULTING

(57) ABSTRACT

Example methods and apparatuses of controlling a user interface with a plurality of input mechanisms are disclosed. One example method includes causing a first set of input mechanisms in the plurality of input mechanisms to be visually emphasized via a first visual technique while a second set of input mechanisms in the plurality of input mechanisms is not visually emphasized via the first visual technique, receiving a user input via an input mechanism that is included in the first set, based on the user input, determining a third set of input mechanisms in the plurality of input mechanisms and a fourth set of input mechanisms in the plurality of input mechanisms, and causing the third set of input mechanisms to be visually emphasized via the first visual technique while the fourth set of available input mechanisms is not visually emphasized via the first visual technique.

20 Claims, 5 Drawing Sheets

Related U.S. Application Data continuation of application No. 15/957,752, filed on Apr. 19, 2018, now Pat. No. 10,765,889.

(60) Provisional application No. 62/566,301, filed on Sep. 29, 2017.

(51) Int. Cl.

| | |
|---|---|
| H01H 9/16 | (2006.01) |
| H01H 13/02 | (2006.01) |
| H01H 13/70 | (2006.01) |
| H05G 1/56 | (2006.01) |
| H05G 1/58 | (2006.01) |
| A61B 6/04 | (2006.01) |
| A61B 17/00 | (2006.01) |
| H03K 17/18 | (2006.01) |
| H03K 17/955 | (2006.01) |
| H03K 17/96 | (2006.01) |

(52) U.S. Cl.

CPC ... *H01H 2300/038* (2013.01); *H01H 2300/04* (2013.01); *H03K 17/18* (2013.01); *H03K 17/955* (2013.01); *H03K 17/96* (2013.01); *H03K 17/962* (2013.01)

(56) References Cited

U.S. PATENT DOCUMENTS

| | | | |
|---|---|---|---|
| 6,069,932 A * | 5/2000 | Peshkin | A61B 34/70 |
| | | | 378/42 |
| 10,765,889 B2 | 9/2020 | Koehl et al. | |
| 11,247,072 B2 | 2/2022 | Filiberti | |
| 2007/0273697 A1 | 11/2007 | Zaman et al. | |
| 2012/0109608 A1 * | 5/2012 | Core | A61N 5/1067 |
| | | | 703/6 |
| 2012/0195407 A1 | 8/2012 | Nenoki et al. | |
| 2012/0314841 A1 | 12/2012 | Heid | |
| 2013/0221243 A1 | 8/2013 | Perkins | |
| 2013/0331635 A1 * | 12/2013 | Hoffman | A61M 39/20 |
| | | | 600/4 |
| 2016/0015340 A1 | 1/2016 | Nenoki et al. | |
| 2016/0081650 A1 | 3/2016 | Okusu et al. | |
| 2016/0135779 A1 | 5/2016 | Kim et al. | |
| 2016/0220218 A1 | 8/2016 | Zaiki et al. | |
| 2018/0169437 A1 * | 6/2018 | Carpenter | G16H 10/60 |
| 2019/0099621 A1 | 4/2019 | Koehl et al. | |
| 2020/0338366 A1 | 10/2020 | Koehl et al. | |

* cited by examiner

100 ⌐

RT Treatment Room 120

Control Room 130

110 ⌐

101 ⌐

122

150

129

161

126 ⌐

160

124

Couch 123

Couch Positioning
Assembly
128

EPID 125

Treatment Room
Control
Console
127

Remote
Control
Console
132

Image Acquisition
and Treatment
Control Computer
131

UI
Controller
137

110

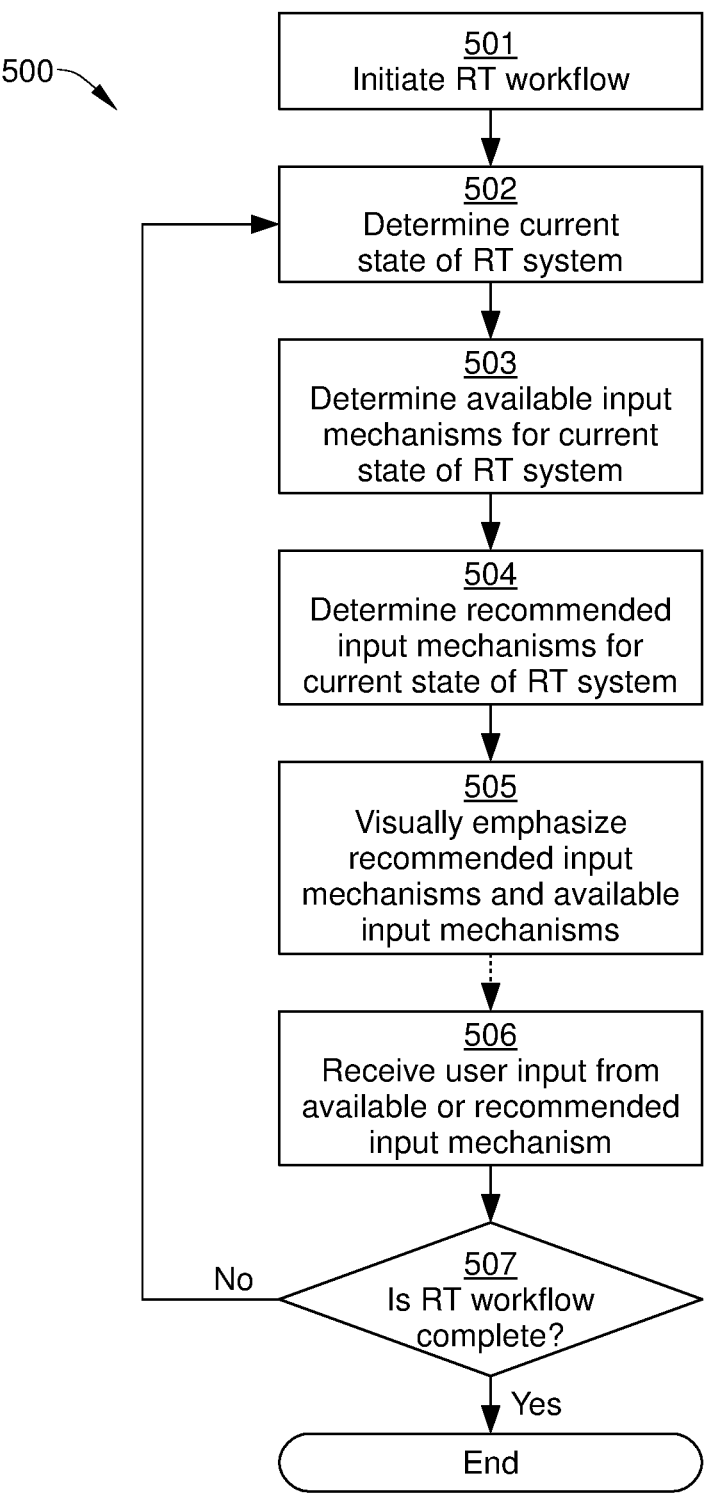

500

501
Initiate RT workflow

502
Determine current state of RT system

503
Determine available input mechanisms for current state of RT system

504
Determine recommended input mechanisms for current state of RT system

505
Visually emphasize recommended input mechanisms and available input mechanisms

506
Receive user input from available or recommended input mechanism

507
Is RT workflow complete?

No

Yes

End

FIG. 5

RADIATION THERAPY SYSTEM WITH FOLLOW-THE-LIGHTS USER INTERFACE

CROSS-REFERENCE TO RELATED APPLICATIONS

The present application is a continuation application under 35 U.S.C. § 120 of U.S. application Ser. No. 16/928,022, filed Jul. 14, 2020, which issued as U.S. Pat. No.11,358,006 on Jun. 14, 2022, which is a continuation application under 35 U.S.C. § 120 of U.S. Application No. 15,957,752, filed Apr. 19, 2018, which issued as U.S. Pat. No. 10,765,889 on Sep. 8, 2020, which claims the benefit of U.S. Provisional Application No. 62/566,301, filed Sep. 29, 2017. The aforementioned U.S. Patents and U.S. Provisional Application, including any appendices or attachments thereof, are hereby incorporated by reference in their entirety.

BACKGROUND

Unless otherwise indicated herein, the approaches described in this section are not prior art to the claims in this application and are not admitted to be prior art by inclusion in this section.

Radiation therapy, which is the use of ionizing radiation, is a localized treatment for a specific target tissue, such as a cancerous tumor. Ideally, radiation therapy is performed on target tissue (also referred to as the planning target volume) that spares the surrounding normal tissue from receiving doses above specified tolerances, thereby minimizing risk of damage to healthy tissue. So that the prescribed dose is correctly supplied to the planning target volume during radiation therapy, the patient should be precisely positioned relative to the linear accelerator that provides the radiation therapy, typically with a movable treatment couch mounted on a turntable assembly. In addition, radiotherapy beams can be shaped around the target tissue to give a high radiation dose to a cancerous tumor while minimizing dosing to the surrounding healthy tissue, thereby reducing the risk of side effects. Furthermore, small changes in the position of the target tissue can be accommodated with image guided radiotherapy (IGRT), in which X-ray scans are employed before and during radiotherapy treatment to determine in real-time the size, shape, and position of the target tissue as well as the surrounding tissues and bones.

A radiation therapy system capable of providing sophisticated treatments like IGRT can be complex to operate, and users generally require extensive training to perform the various workflows on the system efficiently. For instance, performance of patient treatments, system calibration, and other radiation therapy workflows typically involve various functions, inputs, setting adjustments, and motion enable commands. To enable such workflows, a conventional radiation therapy system can have dozens or more different input buttons, switches, scroll wheels, and other input mechanisms for receiving user inputs. Furthermore, a typical radiation therapy workflow usually involves a specific sequence of user inputs selected from this multiplicity of input mechanisms. Consequently, when performing a radiation therapy workflow, selecting the next correct input button or switch from among the dozens of possible input mechanisms available can be problematic and time-consuming. As a result, unless an operator is very experienced with a particular radiation therapy system, utilization of the system will not be maximized, which slows amortization of the system and degrades the radiation therapy experience of the patient.

In light of the above, there is a need in the art for a user interface that facilitates efficient and accurate performance of radiation therapy workflows associated with a radiation therapy system.

BRIEF DESCRIPTION OF THE DRAWINGS

Features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

FIG. 5 sets forth a flowchart summarizing an example method for controlling the user interface of an RT treatment system, according to one or more embodiments of the present disclosure.

DETAILED DESCRIPTION

Figure 1:
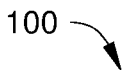
FIG. 1 illustrates a clinical environment in which an embodiment of the present disclosure can be integrated.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

As noted above, when performing a radiation therapy (RT) workflow with an RT treatment system, selecting the next correct input button or switch from among the dozens of possible input mechanisms available to the operator can be problematic and time-consuming. According to various embodiments, while an operator performs a particular workflow that involves the plurality of input mechanisms of an RT system, at each step of the workflow, the operator is assisted in the process of selecting the next input mechanism in a way that greatly reduces the number of possible input mechanisms that can be chosen. Specifically, at each step of the workflow, a first subset of input mechanisms is made visually prominent via a first visual technique and a second subset of the input mechanisms is made visually prominent via a second visual technique. The first subset includes input mechanisms that are available for selection at that particular point in the workflow and the second subset includes recommended input mechanisms that are the most likely to be the next input mechanism that should be actuated by the operator at that particular point in the workflow, as determined by a controller associated with an RT system. For example, in some embodiments, at a particular step in an RT workflow, input mechanisms that are available for selection are illuminated with a first color (e.g., white), the recommended input mechanisms are illuminated with a second color (e.g., blue or green), and input mechanisms that are not available for selection or are otherwise inactive, are not illuminated, or are otherwise made less visually prominent than the other input mechanisms. Thus, in such embodiments, the operator is not required to visually navigate or peruse all the possible buttons and other input mechanisms of the RT system, and instead can immediately determine which input mechanisms are not available in the current step of the RT workflow. Further, illumination of the recommended input mechanisms with a highlight color that is more visually prominent than the available input mechanisms visually presents the operator with a small number of recommended options from which to first consider when selecting the next input mechanism of the RT workflow.

FIG. 1 illustrates a clinical environment 100 in which an embodiment of the present disclosure can be integrated. Clinical environment 100 includes an RT treatment room 120 with an RT treatment system 110 disposed therein and a control room 130, separated by a shielded wall 101. RT treatment system 110 includes a linear accelerator (LINAC) 121 that generates a megavolt (MV) treatment beam 122 of high energy X-rays (or in some embodiments electrons), a patient table or treatment couch 123 mounted on a couch positioning assembly 128, a kilovolt (kV) X-ray source 124, an X-ray imager 150, an MV electronic portal imaging device (EPID) 125 and, in some embodiments, a treatment room control console 127 for controlling RT treatment system 110 and/or couch positioning assembly 128. Control room 130 includes an image acquisition and treatment control computer 131 that is communicatively coupled to X-ray imager 150 and LINAC 121. Control room 130 further includes a remote control console 132 for controlling RT treatment system 110.

Also shown in FIG. 1 is a patient 160, positioned on treatment couch 123 for RT treatment. Patient 160 includes a target region 161. Target region 161 may be, for example, a tumor to receive RT treatment, and can be located in different regions of the body of patient 160, such as the head, thorax, or leg. Typically, couch positioning assembly 128 is configured to position patient 160 so that target region 161 is at or near an isocenter 129 about which LINAC 121, EPID 125, kV X-ray source 124, and X-ray imager 150 are rotated during RT treatment.

LINAC 121 customizes treatment beam 122 to conform to the shape of a tumor in target region 161 of patient 160. Thus, LINAC 121 destroys cancer cells while sparing surrounding normal tissue when the location of target region 161 is precisely known. kV X-ray source 124 is an X-ray source for generating an imaging beam 126, which is directed toward X-ray imager 150 for imaging target region 161 and surrounding areas during RT treatment. For example, in some embodiments, clinical environment 100 is employed for image-guided radiation therapy (IGRT), which uses image guidance procedures for target localization before and during treatment. In such embodiments, the images used to precisely monitor the current location of target region 161 are generated with kV X-ray source 124 and X-ray imager 150. Alternatively or additionally, in some embodiments, images generated with kV X-ray source 124 and X-ray imager 150 can be employed in intensity-modulated radiation therapy (IMRT) applications. In either IGRT or IMRT applications, elements of RT treatment system 110 rotate about treatment couch 123 during RT treatment. For example, in some embodiments, LINAC 121, EPID 125, kV X-ray source 124, and X-ray imager 150 rotate about treatment couch 123 as shown.

Image acquisition and treatment control computer 131 is configured to control operation of RT treatment system 110, including the performance of patient treatments, imager calibrations, assessments of system quality assurance, machine performance checks, and the like. In addition, image acquisition and treatment control computer 131 includes a user interface (UI) controller 137. UI controller 137 is configured to selectively control the visual prominence of input mechanisms (such a buttons or switches) included in treatment room control console 127 and remote control console 132 for receiving inputs from an operator of RT treatment system 110. As a result, UI controller 137 facilitates an operator in performing RT workflows for RT treatment system 110. Specifically, at each step of an RT workflow, UI controller 137 visually indicates which input mechanisms of treatment room control console 127 and remote control console 132 are not available for selection or are otherwise inactive, which can greatly reduce the number of possible input mechanisms from which the operator selects the next input. In addition, at each step of an RT workflow, UI controller 137 visually indicates which input mechanisms are available to receive an input from the operator, and visually highlights which input mechanism or mechanisms are the most likely to receive an input from the operator at the current step of the RT workflow. UI controller 137 can be implemented as a software program executed by image acquisition and treatment control computer 131, as firmware (not shown) associated with image acquisition and treatment control computer 131, and/or as any technically feasible hardware unit capable of performing embodiments of the disclosure described herein, such as a CPU, an application-specific integrated circuit (ASIC), a field programmable gate array (FPGA), any other type of processing unit, or a combination of different processing units.

In the embodiment illustrated in FIG. 1, clinical environment 100 includes treatment room control console 127 and/or remote control console 132 for receiving inputs from and presenting outputs to an operator of RT treatment system 110. Treatment room control console 127 and remote control console 132 each include a plurality of input mechanisms that enable an operator of RT treatment system 110 to perform various RT work flows and to enable motion of treatment couch 123 along one or more movement axes. For example, in some embodiments, such input mechanisms include mechanical buttons, scroll wheels, toggle switches, and/or slider mechanisms. The input mechanisms of treatment room control console 127 and remote control console 132 can be configured as motion enable switches that, when actively actuated by the operator, cause couch positioning assembly 128 to translate treatment couch 123 along one or more axes of motion. The input mechanisms of treatment room control console 127 and remote control console 132 can also be configured to modify certain settings, energize or de-energize X-ray sources associated with RT treatment system 110, change a current mode of operation of RT treatment system 110, enable or disable LINAC 121 or X-ray imager 150, etc. In some embodiments, modes of operation of RT treatment system 110 include a patient setup mode, a patient treatment mode, a service mode, an imager calibration mode, a machine performance check mode, a system quality assurance mode, and the like. One embodiment of treatment room control console 127 is illustrated in FIG. 2.

Figure 2:
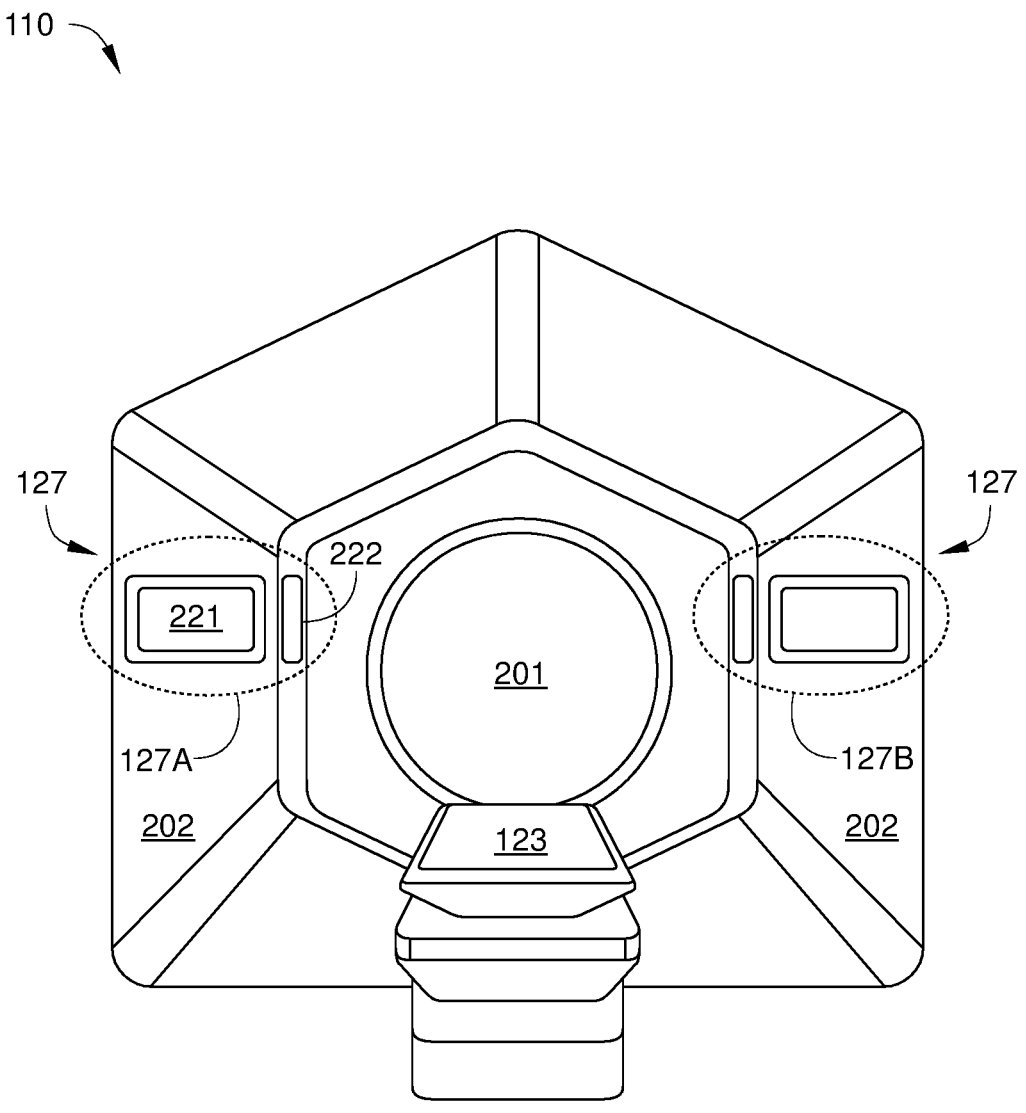
FIG. 2 schematically illustrates a perspective view of a radiation therapy treatment system, according to various embodiments of the present disclosure.

FIG. 2 schematically illustrates a view of RT treatment system 110 that shows treatment room control console 127, according to various embodiments of the present disclosure. In FIG. 2, RT treatment system 110 includes a first instance 127A of treatment room control console 127 on one side of a bore 201 of RT treatment system 110 and a second instance 127B of treatment room control console 127 on the other side of bore 201. Hereinafter, first instance 127A of treatment room control console 127 and second instance 127B of treatment room control console 127 are referred to collectively as treatment room control console 127. In the embodiment illustrated in FIG. 2, treatment room control console 127 is disposed on a vertical surface 202 of RT treatment system 110 and proximate treatment couch 123. Vertical surface 202 can include a stand and/or a vertical panel adjacent to bore 201 of RT treatment system 110. Alternatively, treatment room control console 127 can be located on a hand-held control pendant that is communicatively connected via a wired and/or wireless connection to a controller that receives inputs from the control pendant, such as UI controller 137.

In the embodiment illustrated in FIG. 2, treatment room control console 127 includes a touch-sensitive screen 221 and a control pad 222 that includes a plurality of input mechanisms (not shown for clarity). Touch-sensitive screen 221 can be configured to receive touch-based inputs from an operator, for example via an operator digit or a conductive stylus, and to provide visual outputs to the operator. For example, information-based interactions with RT treatment system 110 can be performed via touch-sensitive screen 221, such as saving images generated by RT treatment system 110, importing treatment plans for implementation by RT treatment system 110, performing data entry related to a particular patient, selecting menu options, etc. By contrast, control pad 222 is a user interface panel that is configured with input mechanisms for use in portions of an RT workflow in which inputs via a mechanical device are required or preferred. For example, in certain RT workflows, positioning of treatment couch 123 is performed by an operator. To prevent unintended motion of treatment couch 123, the input mechanisms of control pad 222 that enable motion of treatment couch 123 are each typically configured as a motion enable switch (also referred to as a "dead man's switch), which is a form of fail-safe device designed to stop the motion or operation of a machine in the absence of an active input from an operator. In addition, the input mechanisms of control pad 222 can include input mechanisms for other functions or for setting adjustments of RT treatment system 110, such as functions that are ill-suited to touch-sensitive screen inputs. For example, in some embodiments, the input mechanisms of control pad 222 can be configured for an operator to make sound volume or lighting adjustments, perform multi-axis control of a patient-monitoring camera, etc. One embodiment of control pad 222 is illustrated in FIG. 3.

Figure 3:
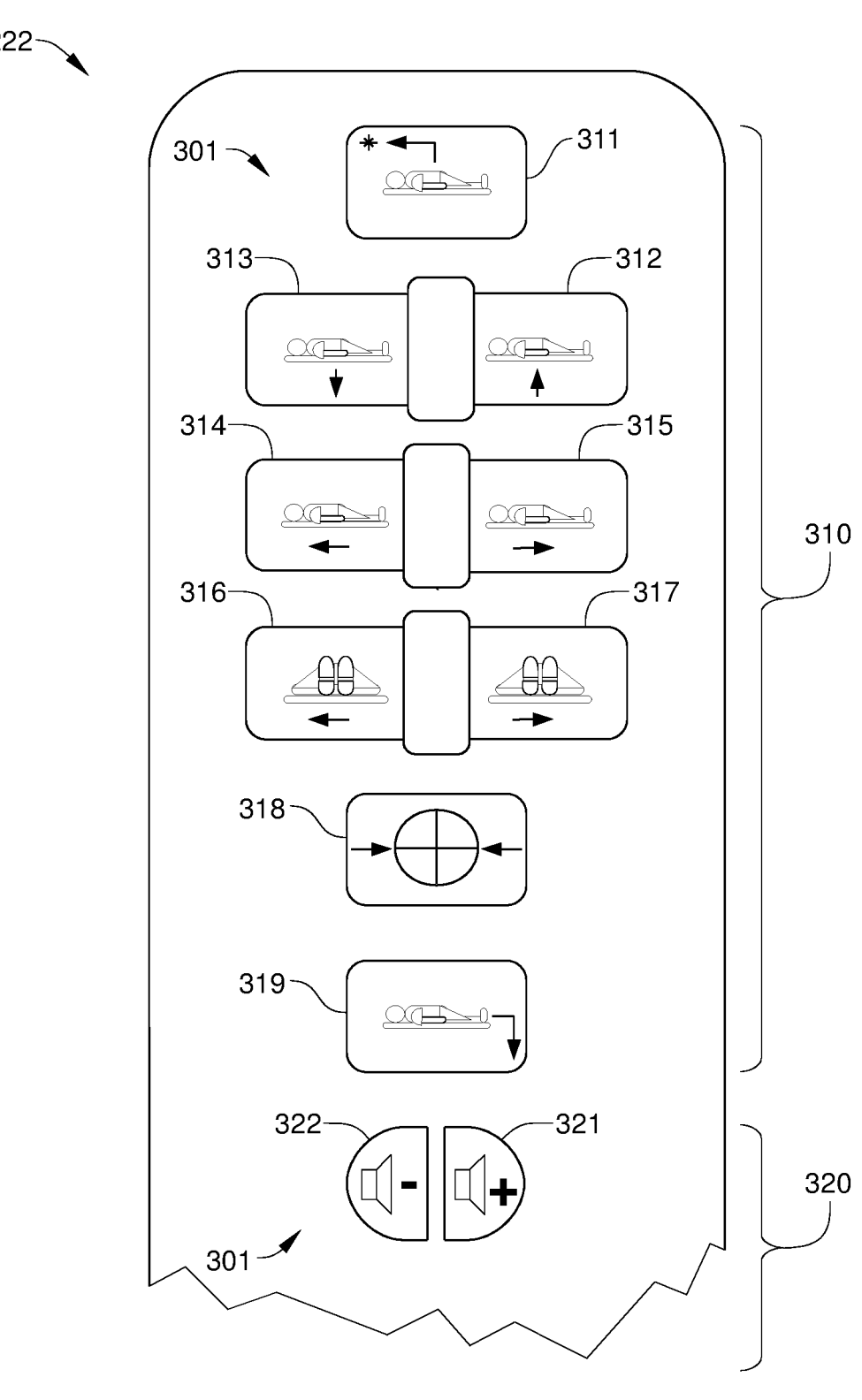
FIG. 3 schematically illustrates a portion of a control pad, according to an embodiment of the present disclosure.

FIG. 3 schematically illustrates a portion of control pad 222, according to an embodiment of the present disclosure. Control pad 222 is a user interface that includes multiple input mechanisms 301 that each generates an input to RT treatment system 110 during an RT workflow. For example, in some embodiments, input mechanisms 310 control motion of a patient couch or other apparatus along one or more axes of motion, and input mechanisms 320 control other functions of RT treatment system 110 and/or can be used by an operator to provide inputs at certain steps in an RT workflow. The one or more axes of motion controlled by input mechanisms 310 can include a vertical, a lateral, and a longitudinal axis of motion. In one such embodiment, certain input mechanisms 310 are buttons configured to initiate preprogrammed motion of a patient couch for RT treatment system 110 along one or more of these axes, while other input mechanisms 310 are buttons configured to enable manual or preprogrammed control of the patient couch along a single axis of motion. In the embodiment illustrated in FIG. 3, control pad 222 includes an alignment button 311 that moves the patient couch to a virtual iso-center of RT treatment system 110, a vertical up button 312 for raising the patient couch, a vertical down button 313 for lowering the patient couch, a longitudinal in button 314 for moving the patient couch into the bore of RT treatment system 110, a longitudinal out button 315 for moving the patient couch out of the bore of RT treatment system 110, a lateral left button 316 for moving the patient couch to the left relative to the bore, a lateral right button 317 for moving the patient couch to the right relative to the bore, a load button 318 for moving the patient couch to the geometric iso-center of RT treatment system 110 (e.g., isocenter 129 in FIG. 1), and a home button 319 for unloading a patient, i.e., for moving the patient couch to a home position of the RT treatment system 110.

In the embodiment illustrated in FIG. 3, input mechanisms 320 include a sound volume increase button 321 and a sound volume decrease button 322, where the sound can include ambient music for a patient and/or an operator voice when speaking to the patient from control room 130. Additionally or alternatively, input mechanisms 320 can include any other suitable input mechanisms for an operator to perform an input during an RT workflow, such as enabling or disabling a function of RT treatment system 110, or changing an operational parameter of RT treatment system 110. For example, input mechanisms 320 can include one or more sliders, scroll wheels, joystick controllers, and the like. Furthermore, in some embodiments, control pad 222 includes more input mechanisms 301 or fewer input mechanisms 301 than those shown in FIG. 3.

Input mechanisms 301 of control pad 222 can be employed by an operator during an RT workflow. An RT workflow for an operator generally includes the sequence of steps and/or inputs that take place in the performance of a particular procedure being performed with RT treatment system 110. There is generally a different workflow for performing a patient treatment, a calibration of X-ray imager 150, a machine performance check (in which the geometric performance of RT treatment system 110 is evaluated), and an assessment of overall system quality assurance, among others. Because each workflow generally includes a different series of inputs from the operator, and because control pad 222 can include dozens of different input mechanisms, locating the next input mechanism in a particular workflow can be a challenge for all but the most experienced operators. According to various embodiments, throughout the performance of a particular workflow on RT treatment system 110, UI controller 137 determines a current state of RT 110, determines which of input mechanisms 301 are available and/or recommended based on the determined state, and causes the available and/or recommended input mechanisms 301 to be made visually more prominent than input mechanisms that are not available or active. Thus, in operation, a first subset of input mechanisms 301 that are determined to be available for selection is made visually more prominent than a subset of input mechanisms that is determined to be unavailable or inactive, and a second subset of input mechanisms 301 is visually highlighted to be more prominent than the first subset of input mechanisms. One such embodiment is illustrated in FIG. 4.

Figure 4:
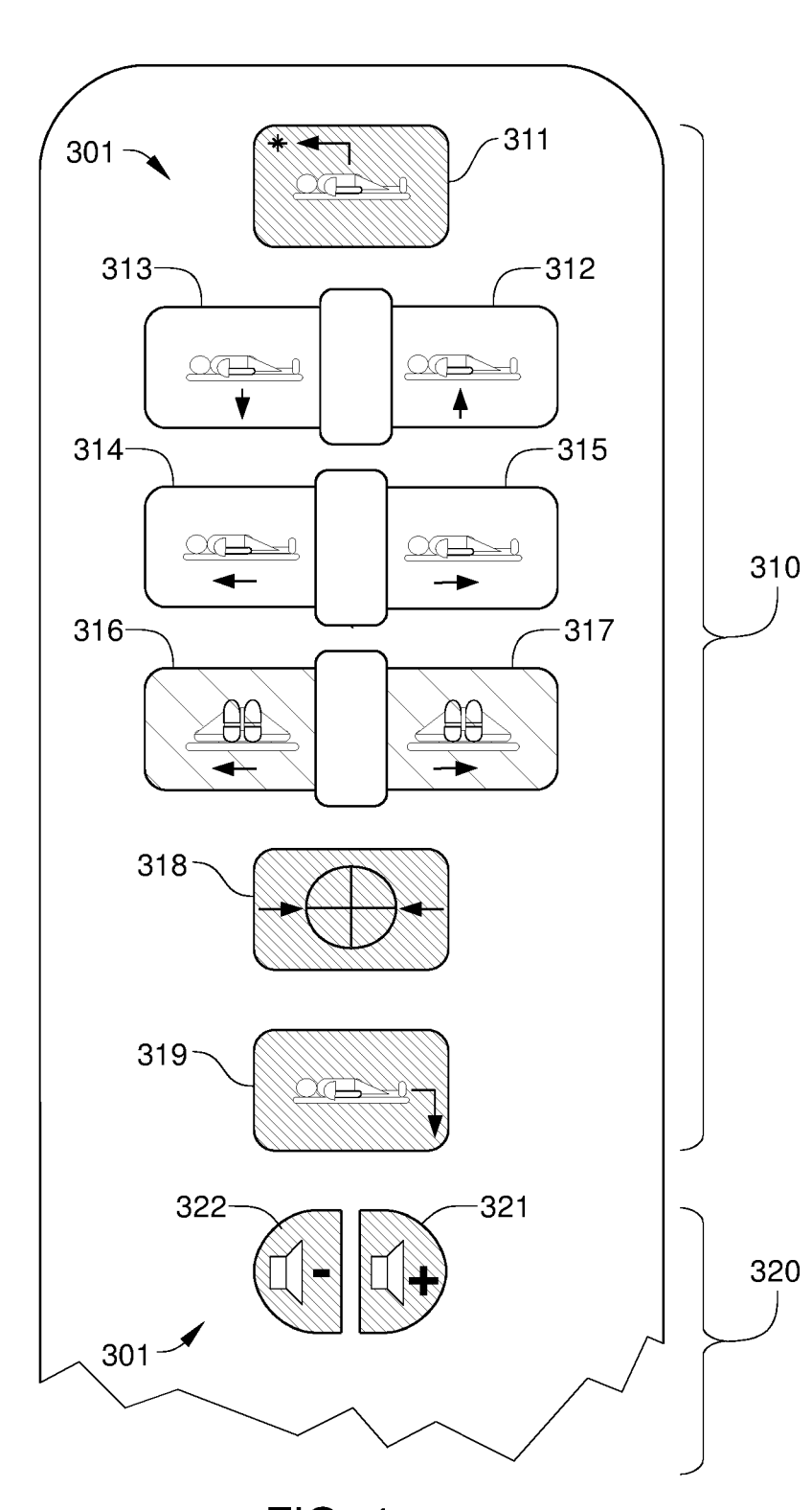
FIG. 4 schematically illustrates a control pad at a certain step of a radiation therapy workflow, according to an embodiment of the present disclosure.

FIG. 4 schematically illustrates control pad 222 at a certain step of an RT workflow, according to an embodiment of the present disclosure. By way of example, the RT workflow is assumed to be a manual positioning workflow, in which target region 161 of patient 160 is manually positioned at a particular location in RT treatment system 110 (target region 161 and patient 160 are both shown in FIG. 1).

At the current step in the workflow, vertical positioning of patient 160 has been completed, for example via vertical up button 312 and vertical down button 313, and longitudinal positioning of patient 160 has been completed, for example via longitudinal in button 314 and longitudinal out button 315. Thus, only lateral positioning of patient 160 remains to be performed. As a result, UI controller 137 determines that the recommended input mechanisms at this point in the RT workflow are lateral left button 316 and lateral right button 317. UI controller 137 further determines that, at this step in the RT workflow, the other available input mechanisms include vertical up button 312, vertical down button 313, longitudinal in button 314, and longitudinal out button 315, while the inactive, unavailable, and/or not applicable input mechanisms include alignment button 311, load button 318, home button 319, sound volume increase button 321, and sound volume decrease button 322. Therefore, UI controller 137 causes the inactive/unavailable input mechanisms of control pad 222 to be made less visually prominent than the other input mechanisms. For example, in some embodiments, UI controller 137 causes alignment button 311, load button 318, home button 319, sound volume increase button 321, and sound volume decrease button 322 to be darkened or not lit (denoted with fine hash marks in FIG. 4). UI controller 137 also causes the available input mechanisms to be visually more prominent than the inactive/unavailable input mechanisms. For example, in some embodiments, UI controller 137 causes vertical up button 312, vertical down button 313, longitudinal in button 314, and longitudinal out button 315 to be illuminated, for example with a white light. UI controller 137 further causes the recommended input mechanisms to be made visually more prominent than any of the other input mechanisms 301 of control pad 322. For example, in some embodiments, UI controller 137 causes lateral left button 316 and lateral right button 317 to be illuminated with a highlight color that is different than and/or more visually prominent than the color of the available input mechanisms, such as blue or green (denoted with coarse hash marks in FIG. 4).

In some embodiments, UI controller 137 determines that a particular input mechanism 301 is an available input mechanism in the current state of RT treatment system 110 the particular input mechanism 301 is associated with a function of RT treatment system 110 that can be performed in the current state. In some embodiments, such a function can typically be performed at a specific step in an RT workflow, but if a certain fault is detected by UI controller 137, UI controller 137 instead determines that the function cannot be performed, and the input mechanism 301 associated with that function is not an available input mechanism. Thus, in such embodiments, a fault status of RT treatment system 110 can effect whether UI controller 137 determines that a particular input mechanism 301 is an available input mechanism or an unavailable/inactive input mechanism. A single or multiple input mechanisms can be determined to be available input mechanisms. To facilitate selection of the next inpu mechanism 301 by the operator, typically, the number of available input mechanisms is greater than the number of recommended input mechanisms.

In some embodiments, UI controller 137 determines that a particular input mechanism 301 is an unavailable or inactive input mechanism in the current state of RT treatment system 110 when the particular input mechanism 301 is associated with a function of RT treatment system 110 that has been disabled or is not applicable in the current state. For example, in some embodiments, when treatment couch 123 (see FIG. 1) has been moved to a maximum vertical position and cannot be moved any higher, UI controller 137 determines that vertical up button 312 is an unavailable input mechanism, and when treatment couch 123 has been moved to a minimum vertical position and cannot be moved any lower, UI controller 137 determines that vertical down button 313 is an unavailable input mechanism. As noted above, a fault status of RT treatment system 110 can also effect whether UI controller 137 determines a particular input mechanism 301 is an unavailable/inactive input mechanism. Further, a current mode of RT treatment system 110 can affect whether UI whether UI controller 137 determines a particular input mechanism 301 is an unavailable/inactive input mechanism. For example, in one embodiment, in a patient setup mode, input mechanisms 301 associated with energizing or enabling X-ray sources of RT system 100 can be inactive input mechanisms, while in a patient treatment mode, the same input mechanisms 301 can be available input mechanisms. A single or multiple input mechanisms can be determined to be unavailable input mechanisms.

In some embodiments, UI controller 137 determines that, in the current state of RT treatment system 110, a particular input mechanism 301 is a recommended input mechanism. In such embodiments, recommended input mechanisms include input mechanisms 301 that are associated with a function of RT treatment system 110 or input to RT system 100 that is more likely to be performed in the current state of RT treatment system 110 than other functions of or inputs to RT treatment system 110. An example of one such function is the next function or input to be performed in the current RT workflow. In some embodiments, a fault status of RT treatment system 110 can effect whether UI controller 137 determines a particular input mechanism 301 is a recommended input mechanism. For example, in response to a particular fault in RT treatment system 110 being detected, there may be a specific input that is typically performed by the operator (such as a patient unload command), and the input mechanism associated with that specific input is selected by UI controller 137 as a recommended input mechanism. A single or multiple input mechanisms can be determined to be recommended input mechanisms.

In the embodiment illustrated in FIG. 4, recommended input mechanisms for a specific step in an RT workflow are made more visually prominent than other input mechanisms via different lighting colors for the recommended input mechanisms and for the available input mechanisms. In other embodiments, any technically feasible technique can be employed for rendering the recommended input mechanisms more visually prominent than the available input mechanisms. For example, in some embodiments, the recommended input mechanisms can be rendered more visually prominent than the available input mechanisms with an additional indicator light (or lights) that is illuminated when the input mechanism is an available input mechanism. Alternatively or additionally, in some embodiments, the recommended input mechanisms can be rendered more visually prominent than the available input mechanisms via a flashing indicator proximate each recommended input mechanism.

In the embodiment illustrated in FIG. 4, available input mechanisms for a specific step in an RT workflow are made more visually prominent than the inactive/unavailable input mechanisms by darkening or not lighting the inactive/unavailable input mechanisms and by lighting the available input mechanisms. In other embodiments, any technically feasible technique for rendering the inactive/unavailable input mechanisms less visually prominent than the available input mechanisms can be employed.

FIG. 5 sets forth a flowchart summarizing an example method for controlling the user interface of an RT treatment system, according to one or more embodiments of the present disclosure. The method may include one or more operations, functions, or actions as illustrated by one or more of blocks 501-507. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with RT system 100 of FIG. 1, persons skilled in the art will understand that any suitably configured system is within the scope of the present disclosure. In the embodiment described in conjunction with FIG. 5, the control algorithms for the method steps reside in and/or are performed by UI controller 137. In other embodiments, such control algorithms may reside in and/or be performed by any other suitable control circuit or computing device.

A method 500 begins at step 501, in which an RT workflow is initiated, for example in response to an input or inputs from an operator of RT treatment system 110. In some embodiments, the input(s) can be received from touch-sensitive screen 221. For example, a mode change or other displayed button may be selected by the operator on touch-sensitive screen 221. Alternatively, the input(s) can be received from an input mechanism 301 of control pad 222.

In step 502, UI controller 137 determines the current state of RT treatment system 110. For example, in some embodiments, UI controller 137 determines whether any faults are currently detected. Alternatively or additionally, in step 502, as part of determining the current state of RT treatment system 110, UI controller 137 determines whether RT treatment system 110 is performing an RT workflow and, if so, what the current step is of the RT workflow. Alternatively or additionally, in step 502, as part of determining the current state of RT treatment system 110, UI controller 137 determines what a current operational mode of RT treatment system 110 is. Alternatively or additionally, in step 502, as part of determining the current state of RT treatment system 110, UI controller 137 determines any other applicable status of RT treatment system 110, such as a current location of treatment couch 123 along each axis of motion, what X-ray sources and other components of RT treatment system are energized or enabled, etc.

In step 503, UI controller 137 determines available input mechanisms of control pad 222 for the current state of RT treatment system 110 determined in step 502.

In step 504, UI controller 137 determines recommended input mechanisms of control pad 222 for the current state of RT treatment system 110 determined in step 502.

In step 505, UI controller 137 causes the available input mechanisms to be visually emphasized via a first visual technique and the recommended input mechanisms to be visually emphasized via a second visual technique that is different than the first visual technique. For instance, in some embodiments, the first visual technique includes lighting each of the available input mechanisms with a suitable respective light, such as a white light or other neutral-colored light, and the second visual technique includes lighting each of the recommended input mechanisms with a respective light having a highlight color, such as blue or green. Alternatively or additionally, in some embodiments, the first visual technique includes lighting each of the available input mechanisms with a respective solid light and the second visual technique includes lighting each of the recommended input mechanisms with a respective flashing light, a significantly brighter light than those employed to illuminate the available input mechanisms, or any other technically feasible light that causes the recommended input mechanisms to be visually distinguishable from the available input mechanisms. Alternatively or additionally, in some embodiments, the recommended input mechanisms are visually highlighted compared to the available input mechanisms, so that the recommended input mechanisms are more visually prominent than the available input mechanisms.

In addition, in some embodiments, in step 504, UI controller 137 also causes the non-available/inactive input mechanisms to be less visually prominent (or otherwise visually de-emphasized) than the available input mechanisms. For example, in some embodiments, UI controller 137 may cause the non-available/inactive input mechanisms to be darkened or unlighted. Thus, the operator can readily distinguish which input mechanisms are not available in the current state of RT treatment system 110.

In step 506, UI controller 137 receives a user input from one of the available input mechanisms or recommended input mechanisms, and RT treatment system responds to the input received accordingly.

In step 507, UI controller 137 determines whether the current RT workflow is completed. If no, method 500 proceeds back to step 502, and UI controller 137 again determines which of input mechanisms 301 are available input mechanisms, recommended input mechanisms, or non-available/inactive input mechanisms; if yes, method 500 terminates. Thus, at each step of an RT workflow, or whenever a change of state of RT treatment system 110 is detected, UI controller 137 changes which input mechanisms of control pad 222 are available, recommended, or unavailable, and caused the input mechanisms to be visually emphasized accordingly.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method of guiding performance of a radiation therapy workflow with a radiation therapy system, the method comprising:

determining a first set of input mechanisms and a second set of input mechanisms based on a first state of the radiation therapy system;

causing the first set of input mechanisms to be visually emphasized via a first visual technique and the second set of input mechanisms to be visually emphasized via a second visual technique that is different than the first visual technique; and

based on a user input via an input mechanism that is included in one of the first set or the second set, determining whether the radiation therapy workflow has been completed.

2. The method of claim 1, wherein each input mechanism in the first set of input mechanisms is associated with a respective function of the radiation therapy system that can be performed by the radiation therapy system when the radiation therapy system is in the first state.

3. The method of claim 1, wherein each input mechanism in the second set of input mechanisms is associated with a respective function of the radiation therapy system that is, when the radiation therapy system is in the first state, more frequently performed than input mechanisms in the first set of input mechanisms.

4. The method of claim 1, wherein causing the second set of input mechanisms to be visually emphasized via the second visual technique comprises causing the second set of input mechanisms to be visually emphasized via the second visual technique while the first set of input mechanisms is visually emphasized via the first visual technique.

5. The method of claim 1, further comprising determining the first state of the radiation therapy system based on at least one of detecting a fault in the radiation therapy system, determining the radiation therapy system is performing a radiation therapy workflow, determining a current operational mode of the radiation therapy system, or determining a mechanical status of the radiation therapy system.

6. The method of claim 5, further comprising determining a current step of the radiation therapy workflow.

7. The method of claim 5, wherein determining the mechanical status of the radiation therapy system is based on at least one of a current location of a treatment couch of the radiation therapy system with respect to one or more axes of motion, an imaging X-ray source of the radiation therapy system being energized or enabled, or a linear accelerator of the radiation therapy system being energized or enabled.

8. The method of claim 1, further comprising, in response to determining that the radiation therapy workflow has not been completed, determining a second state of the radiation therapy system.

9. The method of claim 8, further comprising, based on the second state:

determining a third set of input mechanisms and a fourth set of input mechanisms; and causing the third set of input mechanisms to be visually emphasized via the first visual technique and the fourth set of input mechanisms to be visually emphasized via the second visual technique.

10. The method of claim 8, wherein each input mechanism in the third set of input mechanisms is associated with a respective function of the radiation therapy system that can be performed by the radiation therapy system when the radiation therapy system is in the second state and each input mechanism in the fourth set of input mechanisms is associated with a respective function of the radiation therapy system that is, when the radiation therapy system is in the second state, more frequently performed than input mechanisms in the first set of input mechanisms.

11. The method of claim 1, wherein the first set of input mechanisms and the second set of input mechanisms are included in the radiation therapy system.

12

12. The method of claim 1, wherein the first visual technique comprises illuminating each input mechanism in the first set of input mechanisms with a light.

13. The method of claim 1, wherein causing the second set of input mechanisms to be visually emphasized via the second visual technique causes the second set of input mechanisms to be more visually prominent than the first set of input mechanisms when visually emphasized via the first visual technique.

14. A radiation therapy system, comprising:
a plurality of input mechanisms; and
a controller configured to perform the steps of:
determining a first set of input mechanisms from the plurality of input mechanisms and a second set of input mechanisms from the plurality of input mechanisms based on a first state of the radiation therapy system;
causing the first set of input mechanisms to be visually emphasized via a first visual technique and the second set of input mechanisms to be visually emphasized via a second visual technique that is different than the first visual technique; and
based on a user input via an input mechanism that is included in one of the first set or the second set, determining whether the radiation therapy workflow has been completed.

15. The radiation therapy system of claim 14, wherein each input mechanism in the first set of input mechanisms is associated with a respective function of the radiation therapy system that can be performed by the radiation therapy system when the radiation therapy system is in the first state.

16. The radiation therapy system of claim 14, wherein each input mechanism in the second set of input mechanisms is associated with a respective function of the radiation therapy system that is, when the radiation therapy system is in the first state, more frequently performed than input mechanisms in the first set of input mechanisms.

17. The radiation therapy system of claim 14, wherein causing the second set of input mechanisms to be visually emphasized via the second visual technique comprises causing the second set of input mechanisms to be visually emphasized via the second visual technique while the first set of input mechanisms is visually emphasized via the first visual technique.

18. The radiation therapy system of claim 14, the steps further comprising determining the first state of the radiation therapy system based on at least one of detecting a fault in the radiation therapy system, determining the radiation therapy system is performing a radiation therapy workflow, determining a current operational mode of the radiation therapy system, or determining a mechanical status of the radiation therapy system.

19. The radiation therapy system of claim 14, the steps further comprising, in response to determining that the radiation therapy workflow has not been completed, determining a second state of the radiation therapy system.

20. The radiation therapy system of claim 14, wherein the first visual technique comprises illuminating each input mechanism in the first set of input mechanisms with a light.

* * * * *